(12) United States Patent
Abraham

(10) Patent No.: US 11,027,141 B2
(45) Date of Patent: Jun. 8, 2021

(54) PERICARDIAL IMPLANTABLE CARDIOVERTER DEFIBRILLATOR

(71) Applicant: INNOSCION LLC, San Francisco, CA (US)

(72) Inventor: Theodore P. Abraham, San Francisco, CA (US)

(73) Assignee: INNOSCION LLC, San Francisco, CA (US)

( * ) Notice: Subject to any disclaimer, the term of this patent is extended or adjusted under 35 U.S.C. 154(b) by 283 days.

(21) Appl. No.: 16/016,189

(22) Filed: Jun. 22, 2018

(65) Prior Publication Data

US 2019/0022399 A1 Jan. 24, 2019

Related U.S. Application Data

(63) Continuation-in-part of application No. 15/845,756, filed on Dec. 18, 2017, now Pat. No. 10,772,600, which is a continuation-in-part of application No. 14/865,151, filed on Sep. 25, 2015, now Pat. No. 9,855,021.

(60) Provisional application No. 62/526,170, filed on Jun. 28, 2017, provisional application No. 62/527,865, (Continued)

(51) Int. Cl.
| | | |
|---|---|---|
| A61B 8/14 | (2006.01) |
| A61N 1/39 | (2006.01) |
| A61N 1/368 | (2006.01) |
| A61B 8/12 | (2006.01) |
| A61B 8/08 | (2006.01) |
| A61B 10/04 | (2006.01) |
| A61N 1/05 | (2006.01) |
| A61N 1/375 | (2006.01) |
| A61N 1/37 | (2006.01) |

(52) U.S. Cl.
CPC .......... *A61N 1/3956* (2013.01); *A61B 8/0841* (2013.01); *A61B 8/12* (2013.01); *A61B 10/04* (2013.01); *A61N 1/368* (2013.01); *A61N 1/0502* (2013.01); *A61N 1/0504* (2013.01); *A61N 1/0587* (2013.01); *A61N 1/3704* (2013.01); *A61N 1/37512* (2017.08); *A61N 1/3925* (2013.01); *A61N 1/3975* (2013.01)

(58) Field of Classification Search
None
See application file for complete search history.

(56) References Cited

U.S. PATENT DOCUMENTS

| | | | |
|---|---|---|---|
| 5,052,407 A * | 10/1991 | Hauser | A61N 1/0587 607/125 |
| 8,038,622 B2 | 10/2011 | Abraham | |
| 8,147,413 B2 | 4/2012 | Abraham | |

(Continued)

*Primary Examiner* — Joel F Brutus
(74) *Attorney, Agent, or Firm* — Brown Rudnick LLP; Adam M. Schoen

(57) ABSTRACT

A pericardial implantable cardioverter defibrillator (ICD) may be delivered to the heart through the chest wall using an ultrasound image guided catheter. The ICD may comprise a patch and wire leads which may be secured by a clam shell-like pad at a distal end and comprise a pig-tail shaped securing tail at the other end so that the ICD is firmly attached to the pericardium of a human heart. The ICD may be attached where most needed and serve as either a pacemaker or a defibrillator. In one embodiment, the ICD may emit radio frequency warning signals of heart failure sensed when pacemaker or defibrillator usage is rendered necessary.

18 Claims, 9 Drawing Sheets

Related U.S. Application Data filed on Jun. 30, 2017, provisional application No. 62/590,464, filed on Nov. 24, 2017.

(56) References Cited

U.S. PATENT DOCUMENTS

| | | | |
|---|---|---|---|
| 8,147,414 B2 | 4/2012 | Abraham | |
| 2002/0019629 A1* | 2/2002 | Dietz | A61B 18/1477 |
| | | | 606/41 |
| 2004/0138526 A1* | 7/2004 | Guenst | A61B 17/0218 |
| | | | 600/114 |
| 2009/0299447 A1* | 12/2009 | Jensen | A61N 1/0587 |
| | | | 607/130 |
| 2012/0221072 A1* | 8/2012 | Fukamachi | A61N 1/36139 |
| | | | 607/18 |
| 2013/0066399 A1* | 3/2013 | Min | H01Q 1/2225 |
| | | | 607/59 |
| 2014/0142366 A1* | 5/2014 | Forsell | A61M 1/1048 |
| | | | 600/16 |
| 2016/0081658 A1 | 3/2016 | Abraham | |

* cited by examiner

PERICARDIAL IMPLANTABLE CARDIOVERTER DEFIBRILLATOR

This application claims the right of priority to U.S. Provisional Patent Application Ser. No. 62/527,685 of the same title and by the same inventor filed Jun. 30, 2017 and is a continuation-in-part of U.S. patent application Ser. No. 15/845,756 filed Dec. 18, 2018, which is a continuation-in-part of U.S. patent application Ser. No. 14/865,151 filed Sep. 25, 2015 by the same inventor (now U.S. Pat. No. 9,855,021 issued Jan. 18, 2018) and U.S. patent application Ser. No. 15/845,756 claims the right of priority to U.S. Provisional Patent Application Ser. No. 62/526,170 filed Jun. 28, 2017 and U.S. Provisional Patent Application Ser. No. 62/590,464 filed Nov. 24, 2017.

TECHNICAL FIELD

The present invention relates generally to medical devices and, more particularly, to a device that functions as a pacemaker and/or an implantable cardioverter defibrillator for detecting heart arrhythmias and regularizing heart rhythm.

BACKGROUND OF THE INVENTION

Over 450,000 individuals die suddenly every year in the United States before they can get to a hospital or in the emergency room. Even if rescued by Cardio Pulmonary Resuscitation (CPR) in the field, survival rates are about 3% if there is more than a few minutes delay in starting CPR after the patient collapses. An implantable cardioverter defibrillator (ICD) has been life-saving in millions of patients since it detects potentially life-threatening heart rhythms and delivers an electric shock to the heart to regularize the rhythm. Modern ICDs also function as pacemakers.

Cardioversion and defibrillation both refer to the administration of an electric shock to the heart to treat arrhythmias. Cardioversion refers to a shock that is synchronized to a specific moment of the cardiac cycle. Cardioversion is used to normalize an irregular heart rate that occurs with atrial flutter, atrial fibrillation or ventricular tachycardia with pulse. Defibrillation, on the other hand, refers to a high-energy electric shock that may be administered at any time and is not synchronized to the heart's rhythm. Defibrillation is typically administered as an emergency resuscitative procedure to restore a normal heartbeat in cases of cardiac arrest, pulseless ventricular tachycardia, or ventricular fibrillation.

Early ICDs were placed surgically in the abdomen with wires attached to the epicardium, or on the surface of the heart. Other types of ICDs were placed under the skin below the clavicle with wires inserted through the subclavian vein into the right side of the heart in the right ventricle.

Early ICDs were associated with several risks. When ICDs are placed in the blood stream and attached to the heart muscle there are concerns about infection, clot formation and wire fracture. Long-term wires adhere to blood vessels, so removing them for complications is challenging and high-risk.

More recently, new devices are placed under the armpit (sub-axillary) with wires only running below the skin. Wireless ICD devices (Nanostim) are small capsules placed in the ventricle.

Wired internal devices have risk of blood clots, blood stream infection and wire fracture. They are longer lasting and can pace the heart.

Sub-cutaneous devices do not have any wires going into the heart so there is no chance of clot, blood stream infection or wire fracture. However, they are larger, shorter shelf life, cannot pace the heart, and need to deliver a larger shock when needed.

Certain new small devices are placed inside the ventricle of the heart. Internal nano devices are placed inside the heart but they lack wires, so there is no chance of clots, blood stream infection, or wire fracture while the device is in place. However, since the device is inside the heart, if there are problems with the device and the device must be removed, there is a small chance of clots, malfunction and difficulty removing the device.

The present invention has several advantages over existing ICDs. The present invention is a relatively small device because its battery needs are closer to older versions of ICDs. Because the device is implanted close to the heart, it requires less energy for cardioversion (electrically converting the heart rhythm to normal). The device does not go through the blood stream, so there is no chance of blood clots or infection. The electrode patches may be placed at any location on the heart that needs to be monitored. So, the device can pace either the right or left ventricle and it can defibrillate the ventricles or the atria. The wire moves minimally on the pericardium, so there is little to no chance of wire fracture. The device is easier to remove than existing ICDs. The device is fully deployed using an image guided catheter based delivery system, so there is minimal or no use of X-rays for implanting the device. This is an advantage because of lower costs and less radiation exposure to the patient and the surgeon.

SUMMARY OF THE INVENTION

The present invention is an implantable cardioverter-defibrillator (ICD) and/or pacemaker that monitors the heart rhythm via electrodes, detects abnormalities, and delivers pacing, cardioversion, and/or defibrillation when appropriate. The device may also comprise additional diagnostic technologies, such as ultrasound to detect fluid, biochemistry diagnostics such as, for example, Raman spectroscopy, and/or a mechanism for detecting ST elevation for early detection of a myocardial infarction.

The proposed invention includes a multi-component/multi-device platform that will provide a single, integrated platform for delivery of the ICD into the heart with real-time ultrasound and other image guidance. In an image-guided catheter such as represented by U.S. Pat. No. 9,149,257 entitled "Image Guided Catheters and Methods of Use" issued Oct. 6, 2015 (the '257 patent) by the same inventor, per FIG. 3A, an ultrasound beam generated by a transducer element 210 of an ultrasound imaging channel 214 provides a cone-shaped imaging zone 301 which can display a needle 208 or guide wire or sheath or other tool extending from the distal (patient) end or provide device delivery and be directed parallel to the ultrasound beam and may be located within a sheath or lumen or plurality of lumens. (The '257 patent should be deemed to be incorporated by reference as to its entire contents). On the other hand, the needle 208, a guide wire, sheath, delivery system for a filter or a prosthesis or tool being deployed parallel to the cone-shaped ultrasonic beam imaging zone 301, may be difficult to see in the imaging zone 301 because the needle, guide wire, sheath or lumen is very thin in diameter, may comprise a smooth surface, and may extend in the same direction as the ultrasound beam is projected (parallel to the sonic beam) from the thin, minimally invasive image-guided catheter limiting the amount of desired ultrasound echo. This can be improved by providing echogenicity by sanding, engraving or otherwise causing ultrasound beams to be reflected back to the source so that the sonic beam will tend to follow the angles of impingement and reflection and are intended to project from the needle, sheath or tool in a direction deeper into, for example, a human body in which the image guided catheter of FIG. 3A is inserted and so may be captured by surface-mounted or implanted ultrasound transducers. The image guided catheter may be inserted by directing an introducer needle through the skin surface and guides the image guided catheter under ultrasound vision to site of interest. Ultrasound waves may be echoed or returned to the ultrasound transducer source or scattered toward the human body surface. Also, it is desirable to visualize the needle, sheath or tool itself (via echogenicity) to determine the direction of its movement within the human body from the point of entry of the human body to an area of interest such as the human heart. In one embodiment, the needle or sheath may be hollow (in another, solid) and may be removed or moved forward via a lumen extending the length of the catheter once the catheter is located at a site of interest and may be replaced in real time with a guide wire or tool such as a micromechanical motor system (MEMS). In another embodiment, the tool may be used simultaneously (in its own lumen) with the needle or sheath to bend or guide the needle, guide wire or sheath to the region of interest from a patient's skin surface.

The following additional U.S. Patents and published applications of Dr. Theodore Abraham should be deemed to be incorporated by reference as to their entire subject matter and refer to similar image guided catheters, implanted ultrasound devices, wired or wireless ultrasound devices and the like which may receive signals from echogenic needles, sheaths or tools and surrounding human tissue or blood or other fluids of interest at a site of interest for a minimally invasive surgical procedure: U.S. Pat. No. 8,038,622 issued Oct. 18, 2011; U.S. Pat. Nos. 8,147,413 and 8,147,414, issued Apr. 13, 2012; U.S. Pat. Nos. 8,403,858 and 8,403,859 issued Mar. 26, 2013, and U.S. 2016/008,1658 published Mar. 24, 2016. Most recently, U.S. Ser. No. 15/636,328 entitled "Image Guided Catheters and Methods of Use" was filed by the present inventor on Jun. 28, 2017 and U.S. Provisional Patent Application Ser. No. 62/526,170 entitled "Echogenic Needle, Sheath or Tool" was filed by the present inventor also on Jun. 28, 2017.

The device of the present invention is deployed into the body through the skin using an image guided catheter-based delivery system. The device is attached to either the inside lining or the outside lining of the pericardium. The device can pace the heart's rhythm from either the pericardium or the outside of the heart muscle (epicardium) through a wire attached to the epicardium. It may also function as a defibrillator by delivering an electric shock to the heart to treat life-threatening dysrhythmia.

The ICD/pacemaker of the present invention comprises a wire with one or two coils implanted on the pericardium. At least coil is required for the pacemaker function, while at least two coils are required for defibrillation and cardioversion. The coils function as electric conductors for delivering shocks to the heart. The defibrillation and cardioversion functions of the device are administered by transmitting an electric shock between two coils. The coils also detect electrical energy corresponding to the heart's rhythm and transmit the reading to a microprocessor implanted between the patient's ribs. The microprocessor uses algorithms to detect whether the patient is experiencing a life-threatening arrhythmia. If so, the microprocessor will generate a rhythm for the pacemaker or a signal for the coils to deliver an electric shock to the heart. In a single-coil embodiment of the present invention, one coil is delivered to the pericardium and the microprocessor serves as a second coil.

Coils may be in the form of exposed coiled wire, or in the form of coiled wire embedded inside a patch or wafer comprising a flat piece of metal or plastic. The patch may be a round, square, or rectangular shape.

The wire and coils of the present invention are delivered to the pericardium by an image-guided catheter. The coils, a pericardial pad, and a chest wall pad are pre-loaded and pre-crimped inside of a curved delivery needle, and each component is deployed when the needle is withdrawn out of the body over the wire.

In one embodiment of the present invention, the coils are placed on the visceral (inner) surface of the pericardium. In an alternative embodiment, the coils are placed on the parietal (outer) surface of the pericardium.

To implant the device, an image-guided catheter is inserted through the chest wall and then through pericardium into the pericardial cavity. Then, the delivery needle is advanced into the pericardial cavity through the image-guided catheter. The curved delivery needle is further advanced out of the pericardium at a second site, creating a pathway for the coils to be deployed inside the pericardial cavity.

The delivery needle is then slowly withdrawn back through the catheter, leaving a retention mechanism outside the pericardium. When the needle is withdrawn completely out of the pericardium, the wire remains in place and the coil/patch expands inside of the pericardial cavity. Then, the catheter is withdrawn from the pericardial cavity and the wire is pulled to place the coil immediately adjacent to the inner surface of the pericardium. A pericardial pad is deployed outside of the pericardium to maintain the tension on the wire and keep the coil in close contact with the inner surface of the pericardium.

The needle and the catheter are then withdrawn out of the chest wall, the wire extends out from the chest wall and a pad is deployed outside the chest wall. After exiting the chest wall, the wire with a proximal connector at its end is exposed. The proximal connector plugs into the microprocessor, which in turn receives signals from the coils, and generates a pulse rhythm for the pacemaker function of the device or electric shocks for the defibrillation/cardioversion function. The microprocessor is implanted subcutaneously (under the skin) between the patient's ribs. The microprocessor is powered by a lithium battery, and also detects when the battery is low.

When the device is deployed in the body, the coils are placed near the areas of the heart where the particular patient has problems to monitor those areas. Typically, problems with the ventricles are most likely to be life-threatening, so coils would be deployed near the ventricles to detect any irregular cardiac rhythm in the ventricles. However, some patients have atrial problems. For those patients, the coils would be deployed near the atria.

BRIEF DESCRIPTION OF THE DRAWING

FIG. 1A depicts a round patch, FIG. 1B depicts a square patch, and FIG. 1C depicts a rectangular patch.

FIG. 2A depicts an image guided catheter (also referred to herein as a PeriPort) placed through the pericardium at a first site, with a curved deliver needle extending into the pericardial cavity and out of the pericardium through a second site, and a retaining portion of the wire extending out from the delivery needle.

FIG. 2B depicts the delivery needle being withdrawn into the pericardial cavity out of the second site in the pericardium, deploying the retaining portion and the wire.

FIG. 2C depicts the delivery needle further withdrawn to deploy the coil or patch, which was pre-crimped and pre-loaded on the delivery needle.

FIG. 2D depicts the delivery needle and the catheter completely withdrawn from the pericardial cavity, and the wire pulled or cinched to bring the coil or patch close to the inside of the pericardium.

DETAILED DESCRIPTION

The aspects summarized above can be embodied in various forms. The following description shows, by way of illustration, combinations and configurations in which the aspects can be practiced. It is understood that the described aspects and/or embodiments are merely examples. It is also understood that other aspects and/or embodiments can be utilized, and that structural and functional modifications can be made, without departing from the scope of the present disclosure.

The present invention is an implantable cardioverter-defibrillator (ICD) and/or pacemaker that monitors the heart's activity, detects abnormalities and arrhythmias, and delivers pacing, cardioversion, and/or defibrillation when needed. The device can pace the heart's rhythm from either the pericardium or the outside of the heart muscle (epicardium) through a wire attached to the epicardium. It may also function as a defibrillator by delivering an electric shock to the heart to treat life-threatening dysrhythmia.

The ICD/pacemaker device of the present invention comprises a wire with at least one electrode fastened to the surface of the pericardium. The wire extends out of the pericardium and connects to a microprocessor that is implanted subcutaneously between the patient's ribs. The electrodes of the device may be placed at one or more sites on the pericardium near the areas of the heart that require monitoring. Typically, the electrodes are placed near the ventricles because ventricular arrhythmias are more likely to be life-threatening and require defibrillation. However, for patients with atrial problems, the electrodes may be positioned near the atria to detect any atrial arrhythmias.

Figure 1C:
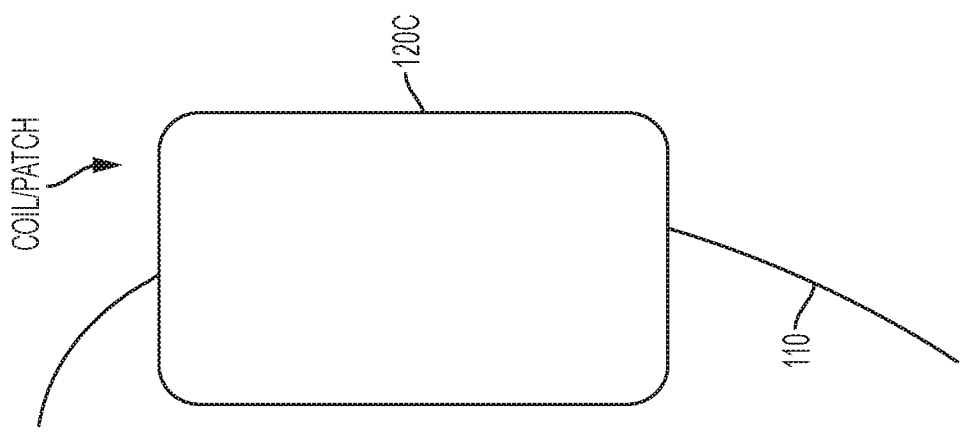
FIG. 1A, FIG. 1B, and FIG. 1C depict the harness, wire, and coil/patch of the present invention.
Figure 1B:
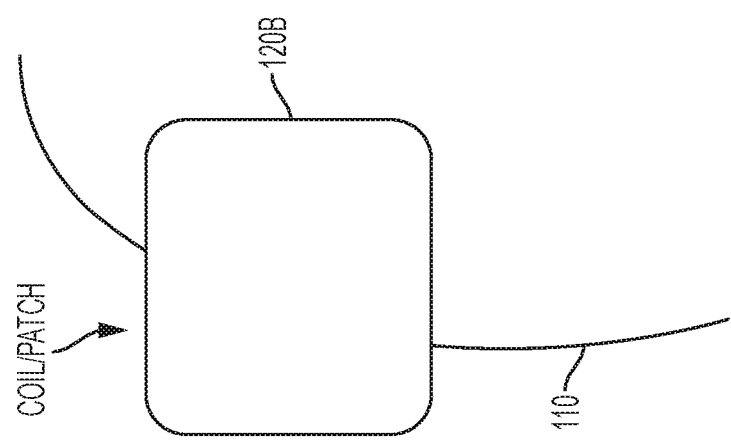
Figure 1A:
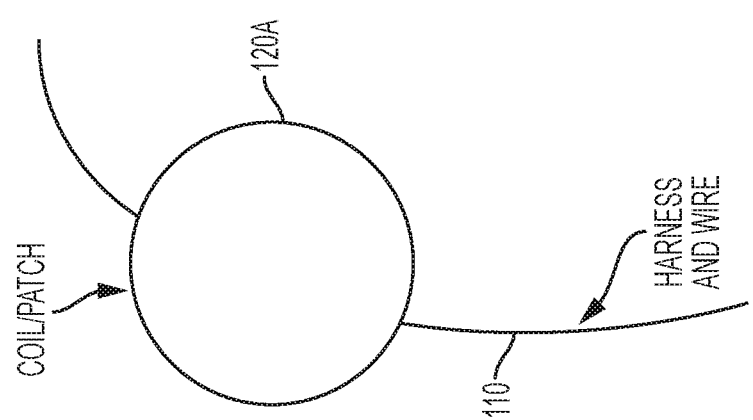

Referring to FIG. 1A, an electrode in the form of a circular patch 120A is shown attached to a wire 110 and harness (not shown). In FIG. 2B, the electrode appears in the form of a square patch 120B. In FIG. 2C, the electrode appears in the form of a rectangular patch 120C. The electrodes may comprise a flat metal patch or a plastic patch with a coil, metal, or other conducting element embedded inside the patch, in various shapes including but not limited to those depicted in FIG. 1A, FIG. 1B and FIG. 1C. The electrode may also consist of a stand-alone metallic wire coil that is not embedded in a flat patch (not shown). The electrode 120 may be interchangeably referred to herein as a coil, a patch, or an electrode and it should be understood that these terms refer to the same component of the present invention.

The patch 120 may also comprise additional diagnostic technologies, such as ultrasound elements which may, for example, detect fluid or a pressure transducer. The patch 120 may further comprise biochemistry diagnostics such as, for example, Raman spectroscopy, and/or a mechanism for detecting ST elevation for early detection of a myocardial infarction.

The wire and coil/patch of the present invention are delivered to the pericardium by an image-guided catheter-based delivery system. The coil/patch, a pericardial pad, and a chest wall pad are pre-loaded and pre-crimped inside of a curved delivery needle, which is introduced into the pericardium through an image-guided catheter, also referred to herein as a Peri-Port. The delivery needle threads the wire, harness, electrode and pads through an entry site and an exit site on the pericardium. The device is then deployed when the needle is withdrawn out of the body over the wire.

FIG. 2A, FIG. 2B, FIG. 2C, and FIG. 2D depict the procedure for delivering a wire and electrode to the inner (visceral) surface of the pericardium closes to the heart. It should be understood, however, that the electrodes of the present invention may be deployed on either the visceral surface of the pericardium or the outer (parietal) surface. The procedure is shown in these figures by way of example, and it may be modified to deliver the device to the parietal surface of the epicardium.

Figure 2A:
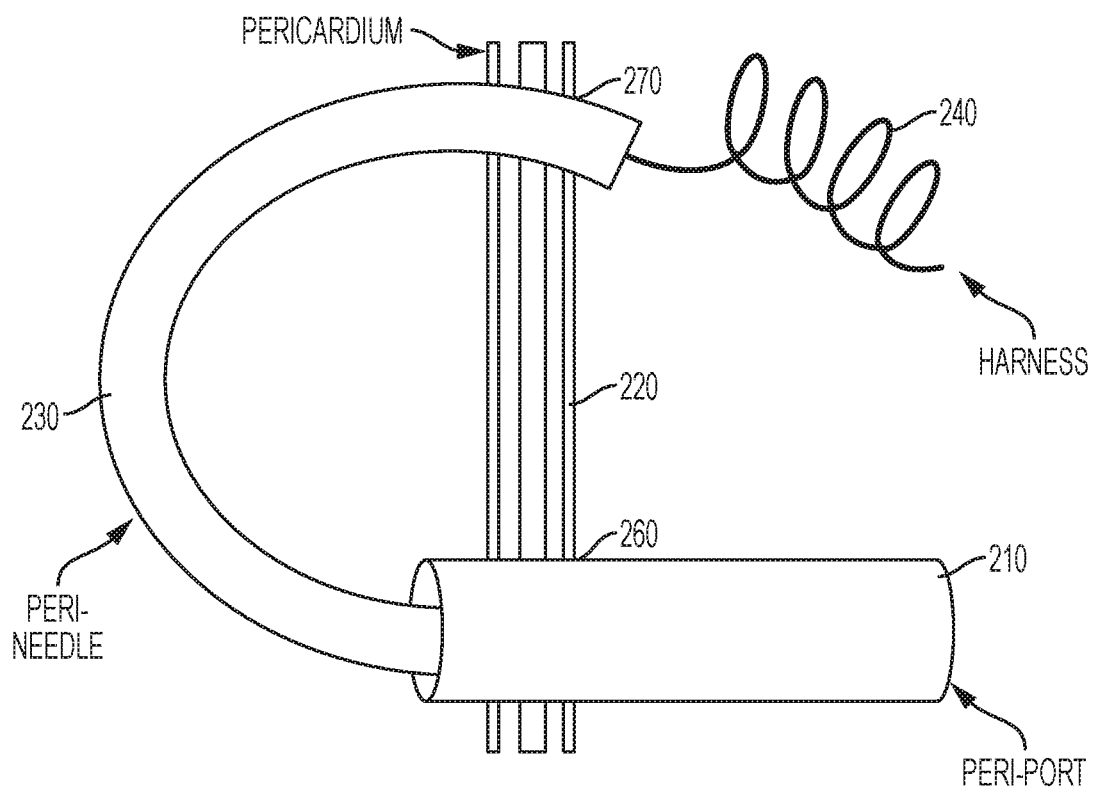
FIG. 2A, FIG. 2B, FIG. 2C, and FIG. 2D show deployment of a patch and wire inside the pericardium via an image-guided catheter and a delivery needle.
Figure 2B:
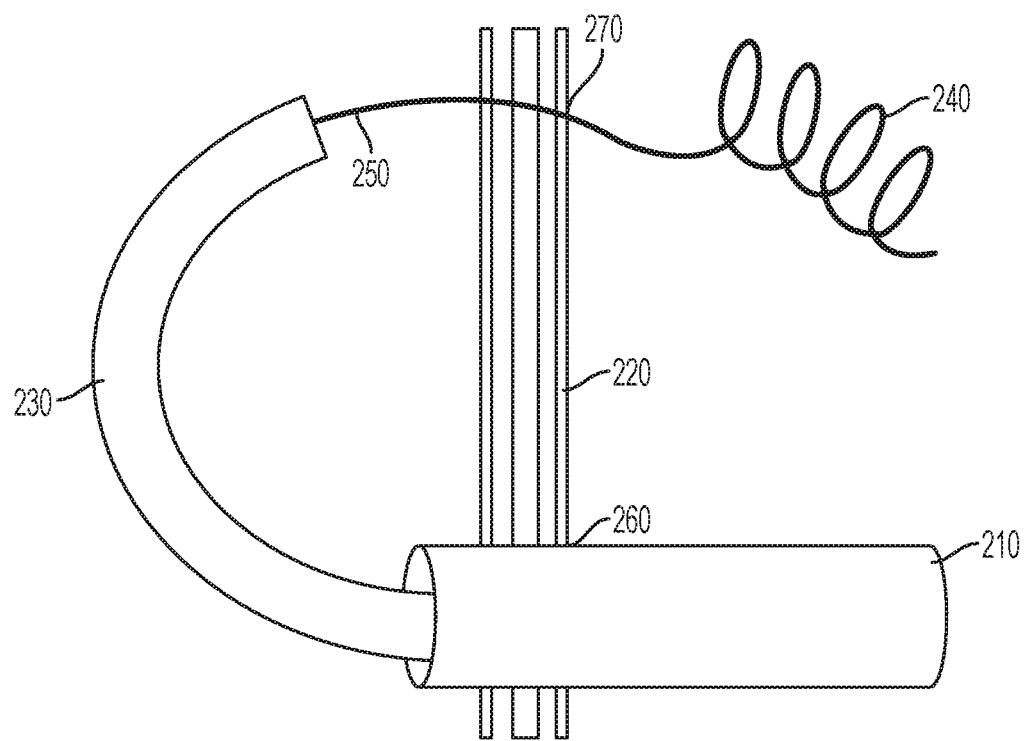
Figure 2C:
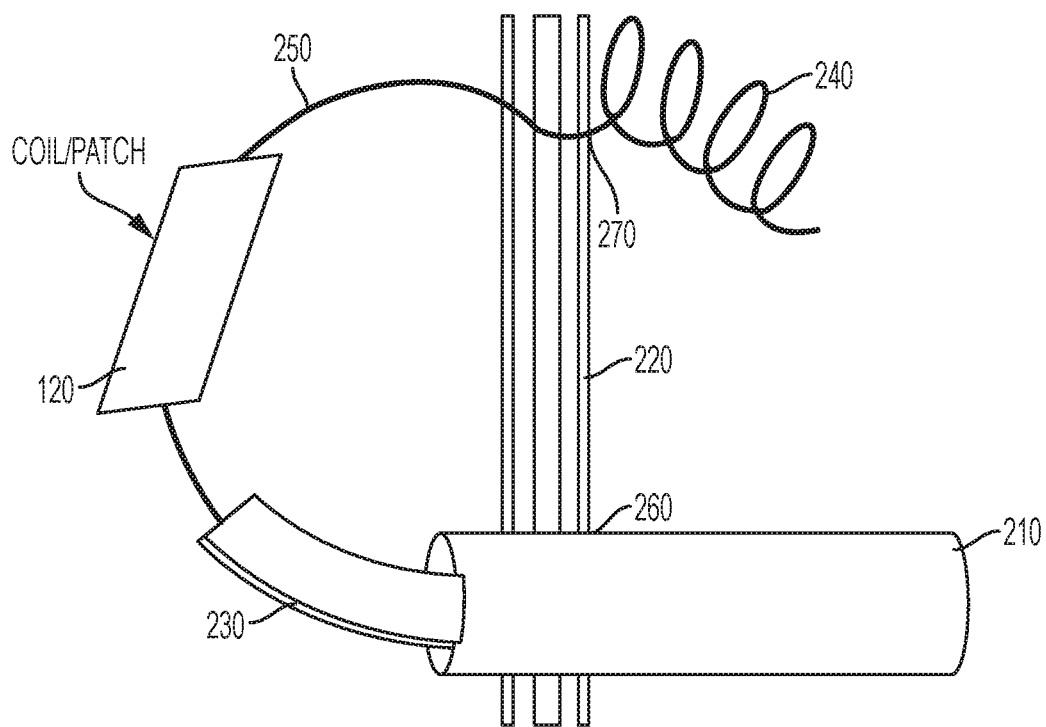

Referring to FIG. 2A, an image-guided catheter (Peri-Port) 210 is introduced first through the chest wall (not shown) and then through an entry site 260 of the pericardium 220. A curved delivery needle 230 is advanced through the Peri-Port and then advanced further through an exit site 270 of the pericardium 220. The curved delivery needle 230 delivers and/or creates a pathway for the harness 240, the wire (not shown), and the patch (not shown) through the pericardium 220. When the delivery needle 230 is withdrawn slightly, the harness 240 is exposed.

As depicted in FIG. 2A, the harness 240 consists of a pigtail wire on the opposite surface from the electrode. The purpose of the harness 240 is to retain the patch or coil on the surface of the pericardium 220. The harness may consist of tines or pigtails as shown in FIG. 2A. The harness 240 may also comprise a hook at the tip of the wire protruding from the exit site 270, with the hook inserted into the pericardium 220 to hold the patch in place. The harness 240 may also comprise a corkscrew or cockscrew that is screwed into the pericardium at the exit site 270 to hold the patch in place. Alternatively, the harness 240 may comprise a clamshell-like coil or patch that is delivered on both sides of the pericardium 220 at the exit site 270.

Referring to FIG. 2B, the delivery needle 230 is slowly withdrawn out of the exit site 270 on the pericardium 220 back into the pericardial cavity, deploying the harness 240 outside the pericardial cavity and further deploying and exposing the wire 250. In an alternative embodiment with a clamshell harness, withdrawing the delivery needle 230 into the pericardial cavity deploys an outer clamshell portion at the exit site 270 on the outer surface of the pericardium 220, and an inner clamshell portion at the exit site 270 on the inner surface of the pericardium 220 such that the clamshell surrounds the pericardium and holds the wire 250 in place.

Referring to FIG. 2C, the delivery needle 230 is further withdrawn to deploy the coil/patch 120 which was pre-crimped and pre-loaded on the delivery needle 230. Withdrawal of the delivery needle 230 covering the coil/patch 120 expands the coil or patch 120 to its final shape.

Figure 2D:
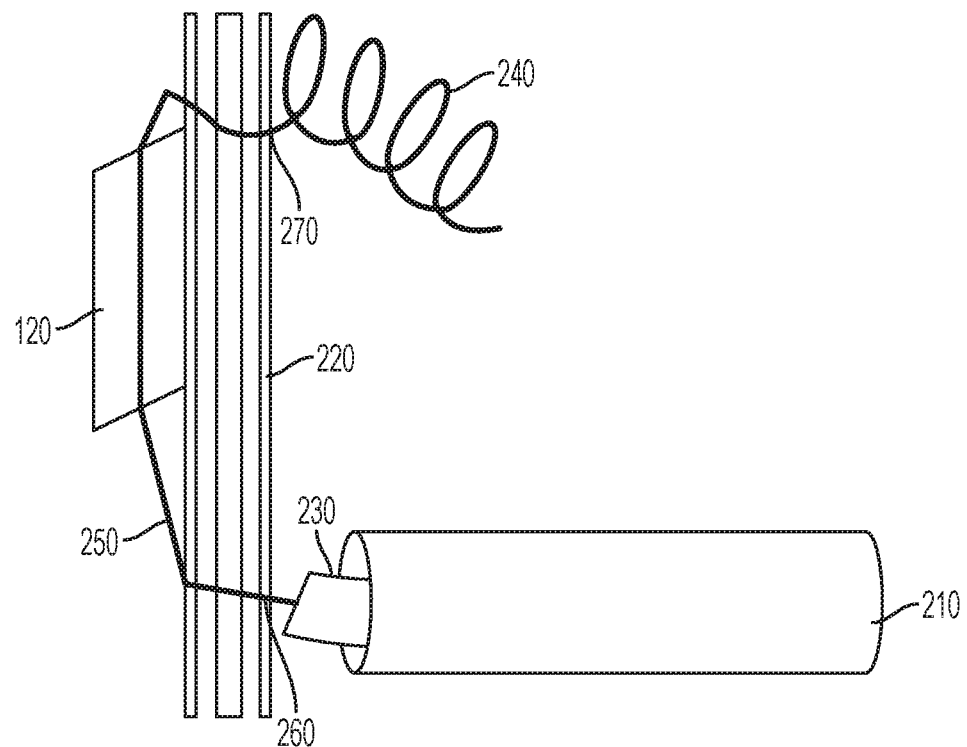

Referring to FIG. 2D, after the coil/patch 120 is deployed, the delivery needle 230 and the Peri-Port 210 are withdrawn from the entry site 260 of the pericardium 220. The harness 240 secures the wire 250 at the exit site 270 of the pericardium 220. After the Peri-Port 210 and the delivery needle 230 are withdrawn from the pericardium 220, the wire 250 is pulled out from the entry site 260 to bring the coil/patch 120 in close proximity to the inner surface of the pericardium 220.

Figure 3A:
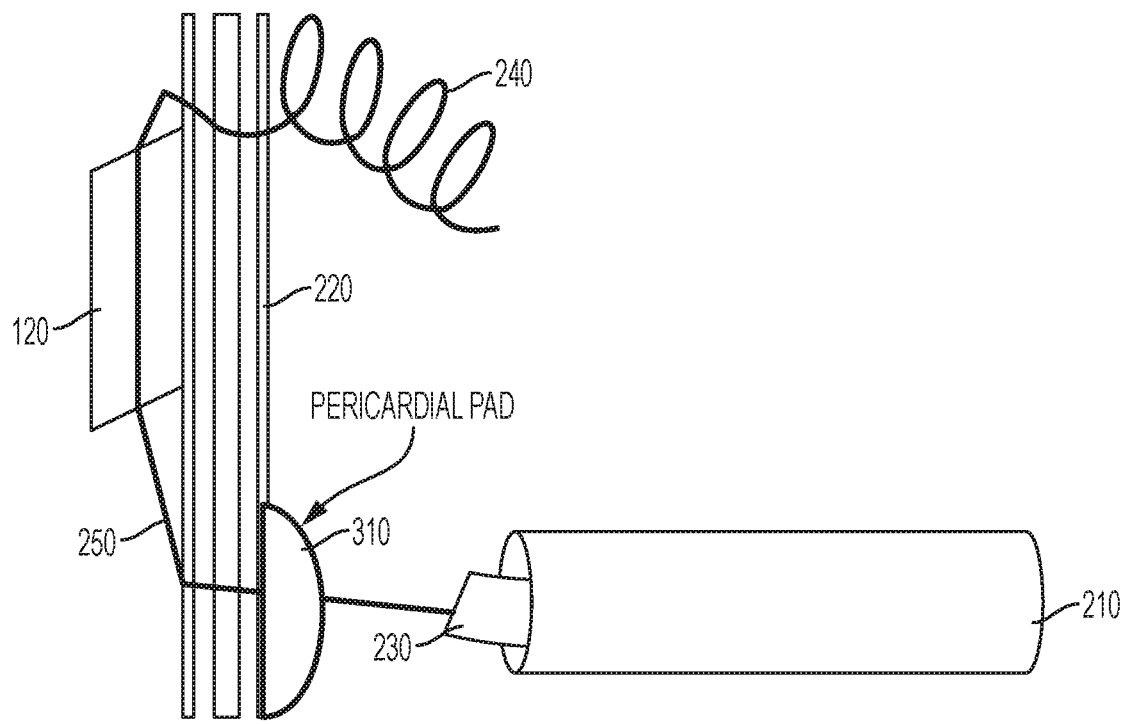
FIG. 3A depicts the pericardial pad, also pre-loaded on the delivery needle, deployed outside of the pericardium.

Referring to FIG. 3A, a pericardial pad 310, also pre-loaded in the delivery needle 230, is deployed on the outer surface of the pericardium 220 by further withdrawing the delivery needle 230. The pericardial pad 310 keeps the tension on the wire and holds the electrode 120 in close contact with the inside of the pericardium.

Figure 3B:
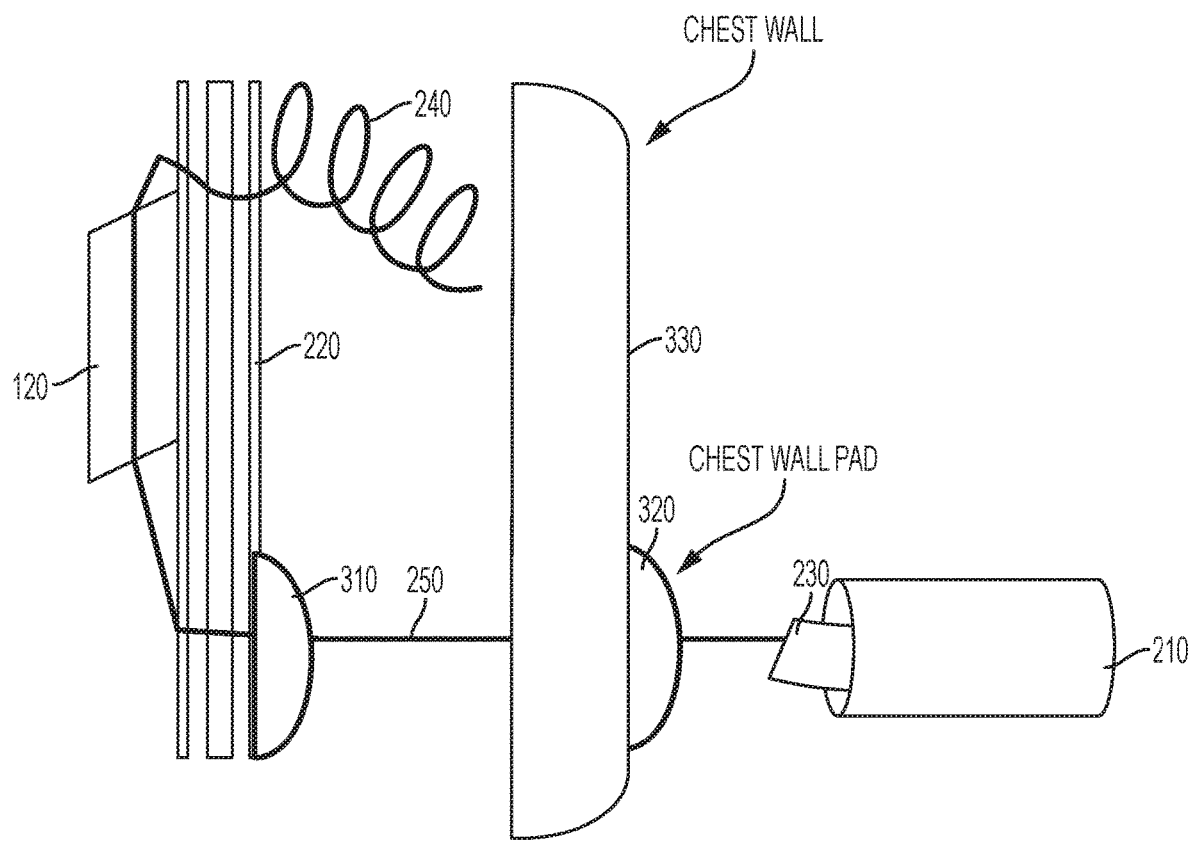
FIG. 3B depicts the device fully deployed in the pericardium, the catheter withdrawn out of the chest wall, and the chest wall pat deployed against the chest wall.

Referring to FIG. 3B, the Peri-Port 210 and the delivery needle 230 are further withdrawn out of the chest wall 330, exposing additional wire 250 as they are withdrawn. After the Peri-Port 210 and the delivery needle 230 exit the chest wall 330, a chest wall pad, also pre-loaded on the delivery needle, is deployed outside the chest wall.

Figure 4:
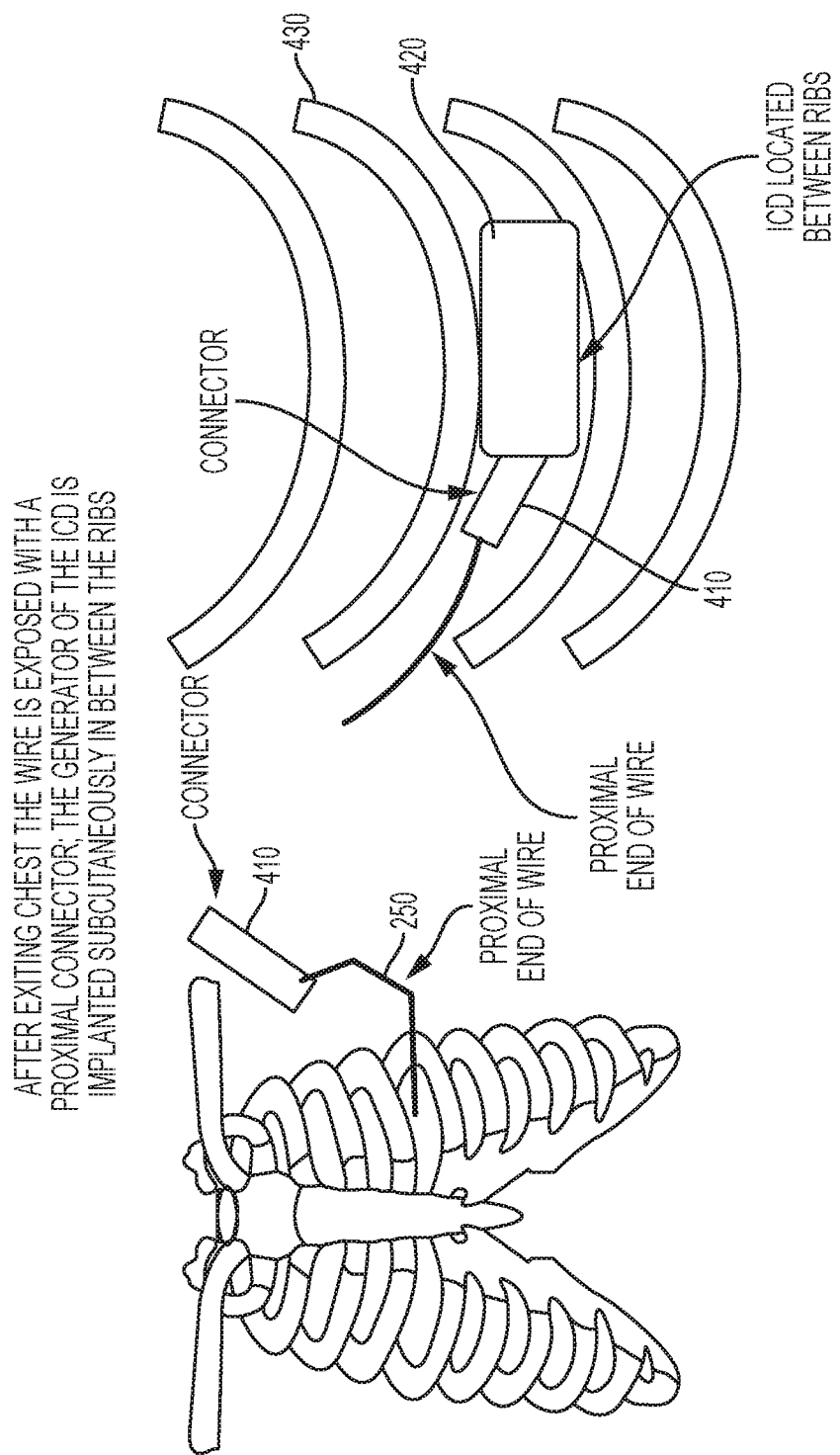
FIG. 4 depicts the wire extending out of the chest wall with a proximal connector, and the proximal connector connected to a microprocessor that is implanted subcutaneously between the ribs.

Referring to FIG. 4, after exiting the chest, the wire 250 is exposed with a proximal connector 410 at its end. The connector 410 plugs into a socket in the microprocessor 420 that is implanted subcutaneously between the ribs 430. Thus, the electrode 120 is connected to the microprocessor 420 through the wire 250, and electrical signals are transmitted between the electrode 120 and the microprocessor 420. The microprocessor 420 may be implanted at different sites between the ribs, either near the apex or axillary. The size of the microprocessor 420 is small and the shape may be altered to conform to the intercostal space.

Figure 5:
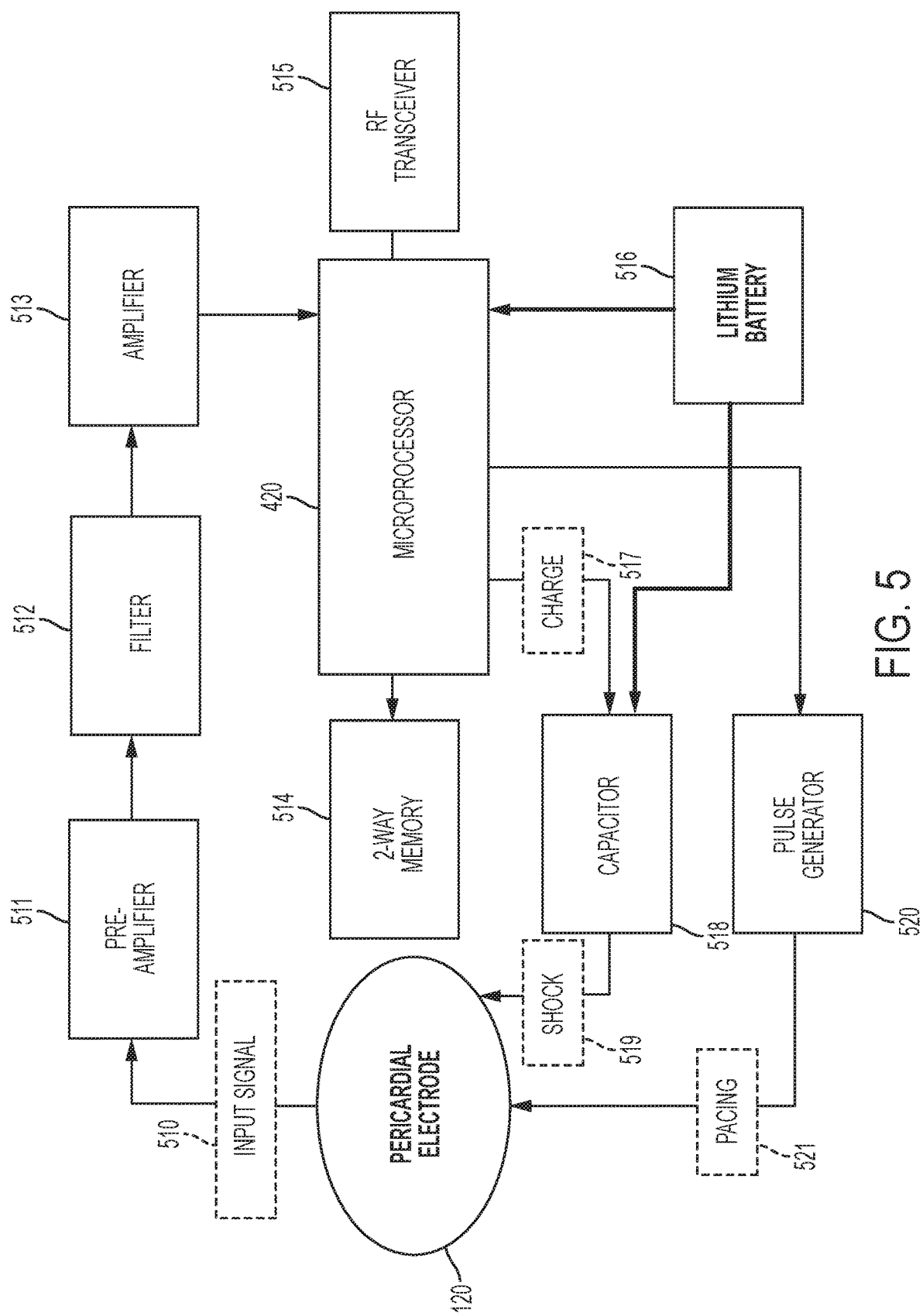
FIG. 5 is a diagram showing the communication pathways between the pericardial electrode, the microprocessor, and the lithium battery.

Referring to FIG. 5, the microprocessor 420 receive signals from the pericardial electrode 120, communicates with the electrode 120 through wires, and controls the pacing and defibrillation/cardioversion functions of the present invention. The pericardial electrode 120 receives electrical signals from a proximal area of the heart indicating its function, then transmits that signal as an input signal 510 to the pre-amplifier 511. The signal is processed by the pre-amplifier 511, the filter 512, and the amplifier 513, and then transmitted to the microprocessor 420. The microprocessor 420 includes a 2-way memory device 514 in which data may be stored, retrieved, and written. Algorithms for detecting cardiac arrhythmias and other abnormalities are stored on the 2-way memory device 514. When the microprocessor 420 received the filtered and amplified signal from the amplifier 513, it analyzes the signal using algorithms retrieved from the 2-way memory 514. The 2-way memory 514 also contains algorithms for determining whether and how to treat an abnormality by administering pacing or a shock to the heart through the electrode 120.

If cardiac arrest or another condition that requires defibrillation or cardioversion is detected, the microprocessor may send a charge 517 to a capacitor 519 which will administer a shock 519 through the electrode 120. Defibrillation is achieved by sending an electric shock between two electrodes 120 or between a single electrode 120 and the microprocessor 420. To achieve the pacemaking function of the device, the microprocessor 420 may generate a pulse 520 to deliver pacing 521 through one or more electrode 120. The microprocessor 420 and capacitor 518 are powered by a lithium battery 516. The microprocessor 420 can detect when the lithium battery 516 is low. The microprocessor 420 further comprises a RF transceiver 515 for receiving and transmitting radio signals. The RF transceiver 515 may alert the patient, the physician, and/or another caregiver when the lithium battery 516 must be replaced. The RF transceiver 515 may also send an alert to the physician and/or caregiver when the patient is experiencing a life-threatening emergency.

The wire and electrode 120 may be deployed at one or more sites on the pericardium as needed, with the wires from each electrode connecting to the microprocessor 420. Multiple coils/wires/patches may be deployed at different sites to get multiple leads for more robust and reliable arrhythmia detection algorithms and capabilities. When the electrode 120 is deployed near the ventricles, the device may provide pacing to a single ventricle or dual ventricles. Electrodes 120 may also be delivered closer to the left or right atrium to allow atrial pacing and atrial defibrillation.

At least one electrode 120 must be deployed in the pericardium to effectuate the device's pacing and defibrillation functions. The electrodes 120 function as conductors for delivering shocks to the heart. The defibrillation and cardioversion functions of the device are administered by transmitting an electric shock between two coils. In an alternative embodiment with only one electrode 120 deployed in the pericardial cavity, the device may administer a shock between the electrode 120 and the microprocessor 420.

All documents mentioned herein are incorporated by reference herein as to any description which may be deemed essential to an understanding of illustrated and discussed aspects and embodiments of devices and methods herein.

Although the devices and methods discussed above and primarily illustrated and described herein provide instruments that also can be adapted for performing minimally invasive diagnostic or therapeutic procedures on humans, it will be appreciated by those skilled in the art that such instruments and methods also are adaptable for use in other surgical procedures as well as in performing various veterinary surgeries. Further, while several preferred embodiments have been described using specific terms, such description is for illustrative purposes only, and it is to be understood that changes and variations may be made without departing from the spirit or scope of the following claims.

The invention claimed is:

1. An apparatus configured to serve as a cardiac pacemaker and/or defibrillator comprising one or more leads, wherein each of the one or more leads is configured to attach to a parietal surface but not to a visceral surface of a pericardium of a heart without entering a heart muscle.

2. The apparatus of claim 1, further comprising a controller.

3. The apparatus of claim 2, wherein the controller communicates with the one or more leads through a wired connection.

4. The apparatus of claim 1, wherein each of the one or more leads comprises at least one coil.

5. The apparatus of claim 4, wherein the at least one coil is arranged within a patch or wafer.

6. The apparatus of claim 1, wherein each of the one or more leads is configured to be deployed from a needle coupled to an ultrasound imaging device.

7. The apparatus of claim 1, wherein the apparatus comprises a single lead.

8. The apparatus of claim 1, wherein the apparatus comprises more than one lead.

9. The apparatus of claim 1, wherein the apparatus comprises a harnessing member.

10. The apparatus of claim 1, wherein the harnessing member comprises a spiraled wire.

11. A method for implanting an apparatus configured to serve as a cardiac pacemaker and/or defibrillator, the method comprising: implanting an apparatus configured to serve as a cardiac pacemaker and/or defibrillator, wherein one or more leads of the apparatus are attached to a parietal surface but not to a visceral surface of a pericardium of a heart without entering a heart muscle.

12. The method of claim 11, wherein implanting is accomplished by deploying the apparatus from within a needle coupled to an ultrasound imaging device.

13. The method of claim 11, wherein the method further comprising connecting the one or more leads to a controller.

14. The method of claim 13, wherein the connection is a wired connection.

15. The method of claim 13, wherein the method further comprises implanting the controller.

16. The method of claim 15, wherein the controller is implanted subcutaneously between ribs of a subject.

17. The method of claim 11, wherein each of the one or more leads comprises at least one coil.

18. The method of claim 17, wherein the at least one coil is arranged within a patch or wafer.

* * * * *